United States Patent [19]
Hu et al.

[11] Patent Number: 5,880,242
[45] Date of Patent: Mar. 9, 1999

[54] NONPOLYMERIC EPOXY COMPOUNDS FOR CROSS LINKING BIOLOGICAL TISSUE AND BIOPROSTHETIC GRAFTS PREPARED THEREBY

[75] Inventors: Can B. Hu, Irvine; Keith E. Myers, El Toro; Diana Nguyen-Thien-Nhon, Santa Ana; Ralph Kafesjian, Newport Beach, all of Calif.

[73] Assignee: Baxter International Inc., Deerfield, Ill.

[21] Appl. No.: 914,558

[22] Filed: Aug. 19, 1997

Related U.S. Application Data

[63] Continuation-in-part of Ser. No. 608,014, Mar. 4, 1996, abandoned.

[51] Int. Cl.⁶ .................................................. A61F 2/24
[52] U.S. Cl. .......................... 527/200; 527/205; 623/1; 623/2; 623/13; 623/15; 623/66
[58] Field of Search .............................. 623/1, 2, 66, 13, 623/15; 527/200, 205

[56] References Cited

U.S. PATENT DOCUMENTS

| | | | |
|---|---|---|---|
| 3,485,573 | 12/1969 | Heyden | 8/94.23 |
| 4,263,680 | 4/1981 | Reul et al. | 3/1.5 |
| 4,624,822 | 11/1986 | Arru et al. | 264/544 |
| 4,687,808 | 8/1987 | Jarrett et al. | 525/54.1 |
| 4,753,652 | 6/1988 | Langer et al. | 623/1 |
| 4,778,461 | 10/1988 | Pietsch et al. | 623/2 |
| 4,798,611 | 1/1989 | Freeman, Jr. | 623/66 |
| 4,806,595 | 2/1989 | Noishiki et al. | 525/54.2 |
| 4,976,733 | 12/1990 | Girardot | 623/11 |
| 5,015,472 | 5/1991 | Isozaki et al. | 424/78 |
| 5,080,670 | 1/1992 | Imamura et al. | 623/2 |
| 5,165,919 | 11/1992 | Sasaki et al. | 424/488 |
| 5,180,789 | 1/1993 | Sasaki et al. | 525/326 |
| 5,296,483 | 3/1994 | Levy | 528/72 |
| 5,296,583 | 3/1994 | Levy | 528/72 |

FOREIGN PATENT DOCUMENTS

| | | |
|---|---|---|
| 60-92762 | 5/1985 | Japan . |
| WO 82/02829 | 2/1982 | WIPO . |
| WO 84/03053 | 8/1984 | WIPO . |
| WO 88/04183 | 6/1988 | WIPO . |

OTHER PUBLICATIONS

Derwent Abstracts 87–074915, "Biocompatible Crosslinked Medical Polymer" Feb. 1987.
Journal of Biomedical Materials Research, vol. 27, pp. 3–9, Mar. 1993.
Denacol Epoxy Compounds—Nagase Chemicals Ltd.
Denacol Epoxy Compounds—Nagase Chemicals Ltd.

*Primary Examiner*—Frederick Krass
*Attorney, Agent, or Firm*—Janice Guthrie

[57] ABSTRACT

A solution containing a nonpolymeric epoxy compound for cross linking biological tissues and bioprosthetic materials prepared thereby. The nonpolymeric epoxy compound has the general structural formula:

$$R_1\text{---}CH_2\text{---}O\text{---}X\text{---}O\text{---}CH_2\text{---}R_2$$

wherein, X is a straight chain aliphatic hydrocarbon having at least four (4) and no more than five (5) carbon atoms bonded directly to one another, said straight chain aliphatic hydrocarbon being devoid of side branches and having terminal carbon atoms at either end thereof, the terminal carbon atoms at the ends of said straight chain aliphatic hydrocarbon being bonded to the oxygen atoms shown in the foregoing general formula, wherein at least one of the terminal groups $R_1$, or $R_2$ is an epoxy group and the other of said terminal groups $R_1$ or $R_2$ is either a) an epoxy group, or b) an aldehyde group. One preferred crosslinking agent of the above general formula is 1,4, butanediol diglycidyl ether. The solution of the present invention contains no other chemical compounds which would react with either collagen or with the crosslinking agent of the present invention.

13 Claims, 2 Drawing Sheets

NONPOLYMERIC EPOXY COMPOUNDS FOR CROSS LINKING BIOLOGICAL TISSUE AND BIOPROSTHETIC GRAFTS PREPARED THEREBY

RELATED APPLICATION

This is a continuation-in-part of U.S. application Ser. No. 08/608,014, filed Mar. 4, 1996, now abandoned.

FIELD OF THE INVENTION

The present invention pertains generally to chemical fixatives which may be used to preserve biological tissue, and more particularly to a group of nonpolymeric difunctional epoxy compounds capable of cross linking biological tissues and the preserved bioprosthetic grafts which are prepared thereby.

BACKGROUND OF THE INVENTION i. Collagenous Biological Tissues Used For Prosthetic Grafting

Various tissues of biological origin have heretofore been used as prosthetic grafts for surgical implantation in or attachment to the body of a human being. As used herein, the term "graft" shall refer to any type of tissue or organ used for subsequent implantation or transplantation, including for example, certain cardiovascular tissues (e.g., segments of blood vessels, heart valves, pericardium), integumentary tissues (e.g., skin), tendons, or other tissues which have been harvested from human or other mammalian sources.

Prior to surgical implantation or transplantation of a graft of biological origin, the graft tissue is typically subjected to a chemical tanning or preservation treatment. The preserved tissue is then stored until it is needed for surgical implantation or grafting into the body of a human patient.

Biological tissues of the type used for allergenic or xenogeneic grafting in human beings (e.g., heart valves, pericardium, blood vessel, skin, etc. . . . ) typically contain a connective tissue matrix. Such connective tissue matrix acts as the supportive framework for the tissue. The cellular parenchyma of the living tissue is disposed within, and supported by, such connective tissue framework.

Collagen and elastin are two substances which make up the connective tissue framework of most biological tissues. The flexibility or rigidity of biological tissue is determined largely by the relative amounts of collagen and elastin present therewithin and/or the physical structure and configuration of the connective tissue framework.

Collagen is a naturally occurring substance which, on a molecular level, consists of three polypeptide chains intertwined in a coiled helical confirmation. The individual amino acid constituents of each polypeptide chain are connected, by way of carbon bonds, to the adjacent amino acids of a neighboring polypeptide chain. Such amino acid bonding serves to hold the polypeptide chains in the triple helical confirmation of the collagen molecule.

Collagenous biological tissues may be tanned or preserved for subsequent surgical grafting and/or implantation by a chemical "fixing" process wherein the collagen network of the graft tissue is exposed to one or more chemical cross linking agents capable of forming chemical cross linkages between the amine groups of the collagen molecules.

The chemical cross linkages formed by the fixative agent include both "intramolecular" and "intermolecular" cross linkages. Intramolecular cross linkages are formed between the amine groups on neighboring polypeptide chains within a particular collagen molecule, while intermolecular cross linkages are formed between amine groups located on different collagen molecules. In general, it is desirable to accomplish substantially complete intramolecular cross linking of collagen within a biological graft material, with only minimal formation of intermolecular cross linkages within such material. Indeed, a high intramolecular cross link density and low intermolecular cross link density is typically associated with the most desirable preservation and physical properties of the resultant biological graft.

ii. Fixative Agents Used to Cross Link Collagenous Tissues

Chemical compounds which are known to be useable as fixatives for cross linking collagen include formaldehyde, glutaraldehyde, dialdehyde starch, hexamethylene diisocyanate and certain polyepoxy compounds.

Polyepoxy compounds which have heretofore been known for use as collagen cross linking agents are described in U.S. Pat. Nos. 4,806,959 (Noishiki et al.) and 5,080,670 (Imamura et al.). At least some of these heretofore-known polyepoxy fixatives are commercially available under the trademark Denacol™ from Nagase Chemicals, Ltd., Osaka, Japan. In particular, one difunctional epoxy compound which has been disclosed for use as a collagen cross linking agent is an ethylene glycol diglycidyl ether based compound commercially available from Nagase Chemicals, Ltd. of Osaka, Japan under the designation Denacol Ex-810. The chemical structure of Denacol Ex-810 is as follows:

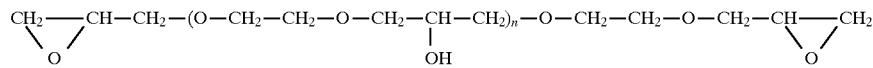

(Denacol Ex-810 is a mixture of congeners wherein n equals 0,1,2 and 3)

As noted, Denacol Ex-810 is actually a mixture of several molecular congeners, each of which has a different molecular weight based on the Number (n) of repeating molecular subunits (represented in the above-shown structural formula) being equal to 0, 1, 2 and 3.

Other epoxy compounds which have been disclosed for use as collagen cross linking agents include those which are commercially available as Denacol Ex-313 and Dencacol Ex-314 from Nagase Chemicals, Ltd. of Osaka, Japan. Denacol Ex-313 and Ex-314 are specifically described in U.S. Pat. No. 5,080,670 (Imamura et al.). Denacol Ex-313 and Denacol Ex-314 are blends of different relative amounts of the following molecular congeners (A–D) as follows:

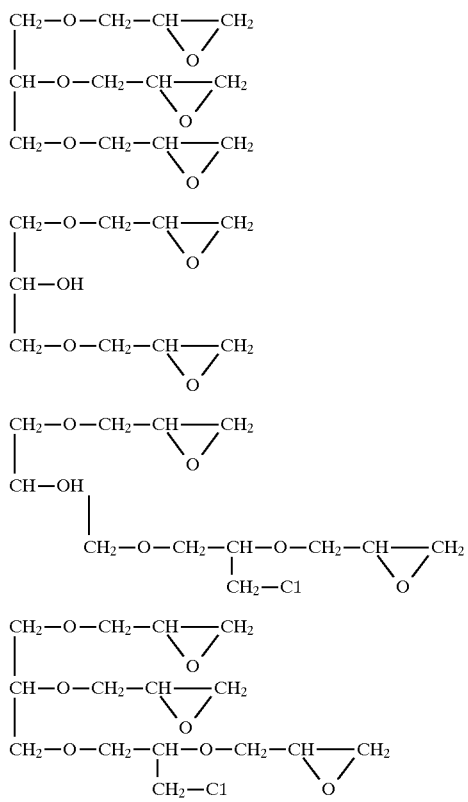

Because Denacol Ex-313 and Ex-314 contain different relative amount of these four (4) molecular congeners (A–D), the average molecular weights and epoxy functionalities of Denacol Ex-313 and Ex-314 differ. The published average molecular weight of Denacol Ex-313 is 270 and its published average epoxy functionality is 2.0. The published average molecular weight of Denacol Ex-314 is 320 and its published average epoxy functionality is 2.3.

In general, cross linking agents of low molecular weight cause relatively fast cross linking of collagen while cross linking agents of high molecular weight are relatively slow acting in this regard. Thus, at a given temperature and pressure, the cross link density or number of cross linkages formed may be affected by both time of exposure of the fixative (i.e., cross linking agent) solution and the molecular weight (or molecular weight distribution) of the particular cross linking agent(s) being used. Additionally, the cross link density or number of cross linkages formed in the collagen network may be affected by other factors including a) the concentration of the cross linking agent in the fixative solution, b) the pH of the fixative solution, and c) any alteration or change in the physical conditions such as temperature and pressure.

One method of assessing the cross link density or relative number of cross linkages formed in a collagenous tissue is by a chemical assay known as the ninhydrin assay. The ninhydrin assay measures the number of unbound amine ($NH_2$) groups present in the collagenous tissue. Since the cross linking agents bind to the amine groups of the collagen molecules, the present number of unbound amine groups is directly indicative of the completeness of the cross linking which has occurred. In this regard, high ninhydrin assay values indicate a relatively incomplete state of cross linking of the collagenous tissue while lower ninhydrin assay values indicate relatively complete cross linking of the collagenous tissue.

iii. Problems and Limitations Associated With Cross Linked Collagenous Grafts

One drawback associated with chemically cross linked collagenous biograft materials is that residual chemical cross linking agent may remain within the graft and may adversely affect the biocompatability and/or tissue affinity of the graft material.

Prior investigators have attempted to deal with this problem by utilizing chemical neuteraliting agents which act to chemically neutralize or deactivate residual or unreacted cross linking agent which is present within the graft. Examples of prior United States patents which describe methods whereby collagenous graft materials are treated with fixative deactivating or neutralizing chemical agents include U.S. Pat. No. 3,974,526 (Dardik) entitled VASCULAR PROSTHESES AND PROCESS FOR PRODUCING THE SAME; U.S. Pat. No. 3,988,782 (Dardik) entitled NON-ANTIGENIC, NON-THROMBOGENIC INFECTION-RESISTANT GRAFTS FROM UMBILICAL CORD VESSELS AND PROCESSES FOR PREPARING AND USING SAME and U.S. Pat. No. 4,553,974 (Dewanjee) entitled TREATMENT OF COLLAGENOUS TISSUE WITH GLUTARALDEHYDE AND AMINO-DIPHOSPHONATE CALCIFICATION INHIBITOR.

In many applications, fixed biograft materials are grafted within the host body in a manner which results in direct contact between specific regions or portions of the graft and certain host tissues. Thus, noncompatability between the graft and the host tissue may give rise to problems with graft biocompatability or graft-host reactions. The amount of fixative chemical present in a particular region, portion or surface of a graft may affect the biocompatibility of that portion or surface of the graft with the adjacent host tissue.

In many applications sufficient bio-affinity is required to enable the tissue graft to undergo endothelialization, (e.g., in situ endothelialization of a vascular graft by way of blood stream regeneration or in vitro endothelialization of a graft surface prior to its surgical implantation). Vascular grafts of biological origin are typically implanted to a host blood vessel by way of end-to-end anastomosis of such that blood will flow directly through the lumen of the graft.

Another problem associated with chemically cross linked collagenous grafts is that the chemical cross linking process may result in stiffening or rigidification of the graft tissue. Such stiffening or rigidification of the graft tissue can cause difficulty in subsequent handling of the tissue to form the desired graft material and/or in the surgical implantation and anastomosis of the tissue to the recipient host.

Yet another problem associated with chemically cross linked collagenous grafts is calcification of the graft following implantation thereof. Such calcification of the implanted graft can be particularly problematic in bioprosthetic heart valve grafts, as such calcification may cause the valve leaflets to become rigid and incapable of performing their intended hemodynamic valving function.

In view of the forgoing problems associated with the chemically cross linked collagenous bioprosthetic graft materials, there remains a need in the art for the development of improved chemical fixative agents which do not cause unacceptable graft-host reactivity and/or which do not undergo unacceptable post-implantation calcification having and/or which do not cause unacceptable stiffening of the cross linked tissue.

SUMMARY OF THE INVENTION

The present invention provides a nonpolymeric epoxy compound in a solution which is usable to cross link collagenous biological materials (e.g., heart valves, pericardium, blood vessels, skin, etc.).

In accordance with the invention, the cross linking solution contains a compound having the general structural formula:

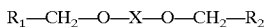

wherein, the molecular backbone X is a straight chain aliphatic hydrocarbon having at least four (4) and no more than five (5) carbon atoms bonded directly to one another, said straight chain aliphatic hydrocarbon being devoid of side branches and having terminal carbon atoms at either end thereof, the terminal carbon atoms at the ends of said straight chain aliphatic hydrocarbon being bonded to the oxygen atoms shown in the foregoing general formula, and wherein at least one of the terminal groups $R_1$, or $R_2$ is an epoxy group and the other of said terminal groups $R_1$ or $R_2$ is either a) an epoxy group, or b) an aldehyde group. The solution of the invention contains no other chemical compounds that would react with collagen or with the epoxy compound described above.

Still further in accordance with the invention, there are provided methods for cross linking collagenous tissues wherein one or more compounds of the general formula described hereabove are dissolved in a liquid solvent, and a collagenous biograft material is then immersed within, or otherwise placed in contact with, such solution for a sufficient period of time to cause the collagenous tissue to become cross linked to a desired cross link density. Examples of the types of collagenous tissues which may be utilized include heart valves, pericardium, blood vessels, tendons, skin, etc.

Still further in accordance with the invention, there are provided fixed biograft articles prepared in accordance with the foregoing method, such articles including but not necessarily limited to cross linked heart valves, pericardium, blood vessels, tendons, skin, etc.

Further objects and advantages of the present invention will become apparent to those skilled in the art upon reading and understanding of the following detailed description of preferred embodiments.

DETAILED DESCRIPTION OF THE PREFERRED EMBODIMENTS

Figure 1:
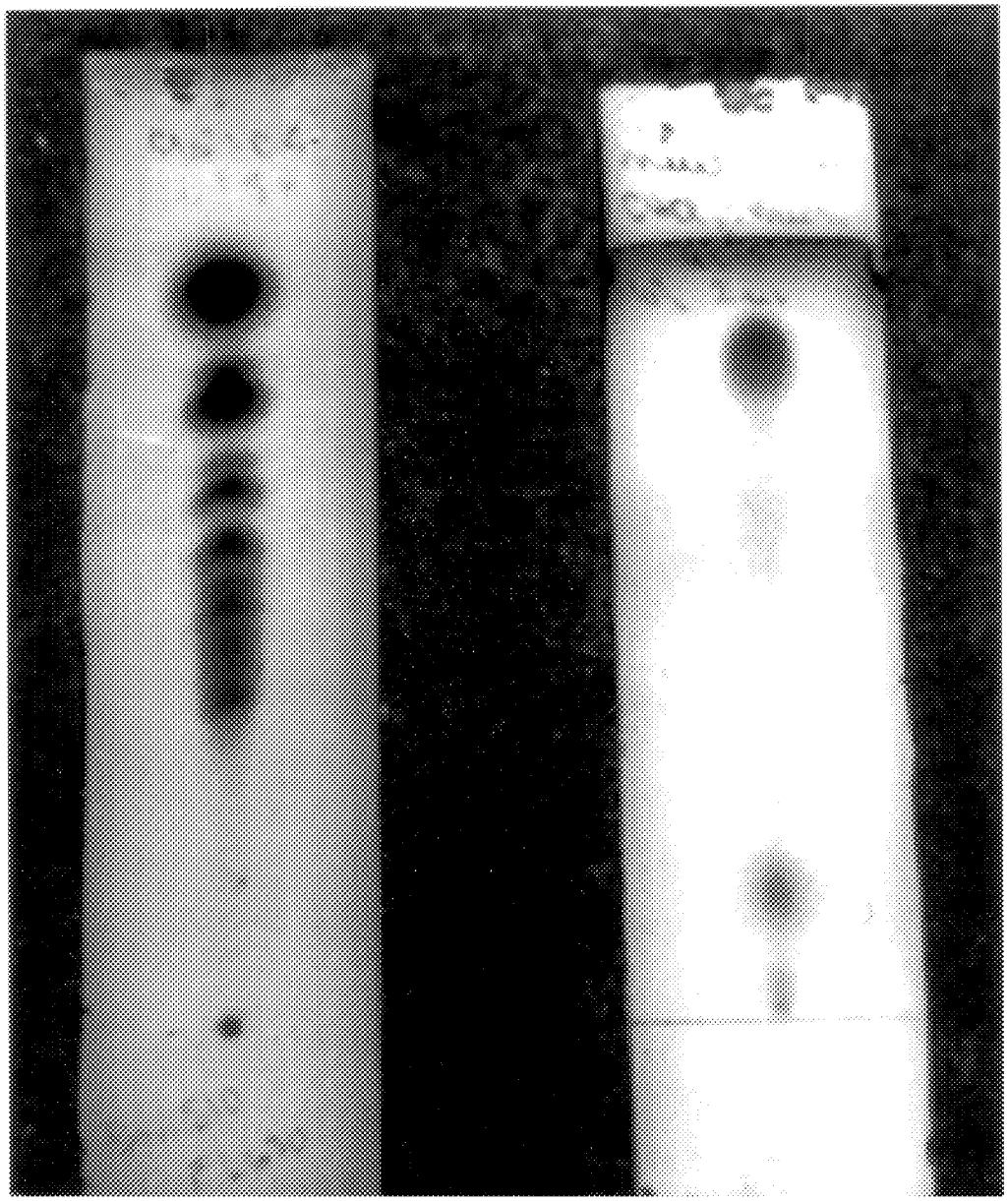
FIG. 1 is a comparison of thin layer chromatographs of the 1,4-butanediol diglycidyl ether compound of the solution of the present invention and Denacol™ 810.

The following detailed description, and the examples articulated therein, is provided for the purpose of describing and illustrating presently preferred embodiments of the invention only, and is not intended to limit the scope of the invention in any way.

The solution for cross-linking collagen, of the present invention, contains a compound of the general structural formula:

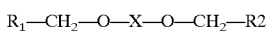

In accordance with this general structural formula, each compound of the present invention has a molecular backbone X, and two terminal groups $R_1$ and $R_2$.

The molecular backbone X comprises an aliphatic hydrocarbon consisting of a straight carbon chain having at least four (4) and no more than five (5) carbon atoms bonded directly to one another, said straight chain aliphatic hydrocarbon being devoid of side branches and having terminal carbon atoms at either end thereof, the terminal carbon atoms at the ends of said straight chain aliphatic hydrocarbon being bonded to the oxygen atoms of the foregoing general formula. The opposite termini or ends of the molecular backbone X are preferably bonded directly to the oxygen atoms of the molecule, as shown in the above-set-forth general formula.

Examples of specific aliphatic hydrocarbons which consist of straight carbon chains of at least four (4) carbon atoms bonded directly to one another which may be utilized as the molecular backbone X include, but are not necessarily limited to, n-butyl (—$CH_2$—$CH_2$—$CH_2$—$CH_2$—) and n-pentyl (—$CH_2$—$CH_2$—$CH_2$—$CH_2$—$CH_2$—). It is preferable that this straight-chain aliphatic hydrocarbon be either 4 or 5 carbon atoms in length, so as to provide a molecule of optimal size for cross linking of collagen. It is further preferable that the straight carbon chain of the aliphatic hydrocarbon be devoid of any side branches which would sterically or otherwise hinder or interfere with the collagen cross linking function of the molecule.

Preferably, the molecular backbone X of the nonpolymeric epoxy compounds of the solution of the present invention will be of a size which results in the functional groups $R_1$ and $R_2$ being spaced apart by a distance which results in intramolecular cross linking between collagen molecules.

At least one of the terminal groups $R_1$, $R_2$, is an epoxy group having the structure

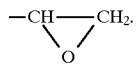

The other of such terminal groups $R_1$, $R_2$, may be either:
a) an epoxy group having the structure

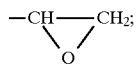

or b) an aldehyde group having the structure

Each collagen cross linking compound having the above-set-forth general formula is formulated in a solution which is substantially devoid of other congeners, molecular fragments, other chemical compounds or impurities which would affect the rate and/or completeness of collagen cross linking by said compound either by reacting directly with the collagen or by reacting with the compound of the present invention.

In many applications, it will be preferable to select collagen crosslinking compounds of the present invention which are soluble in aqueous solution up to at least 40% (v/v) and preferably up to about 10% (v/v).

EXAMPLE I (Preferred Collagen Cross linking Compound of the Present Invention)

The following presently preferred compound of the present invention is soluble in water and usable, in aqueous solution, as a fixative (i.e., cross linking) agent for collagenous biological materials:

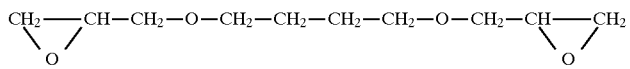

(Chemical Name: 1,4-butanediol diglycidyl ether)

In accordance with this presently preferred compound, the molecular backbone X is an n-butyl group ($-CH_2-CH_2-CH_2-CH_2-$) and the terminal groups $R_1$, and $R_2$, are both epoxy groups

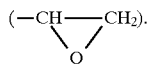

This preferred compound is prepared in a fixative solution which is devoid of any other amine-reactive compounds or congeners or fragments of the above-shown preferred compound having molecular weights or molecular structures which differ from that shown in the above chemical formula for this preferred compound.

This presently preferred compound is soluble in water and is prepared in aqueous solution for fixing of collagenous tissue by immersion of the collagenous tissue within such aqueous solution. The concentration of the 1,4-butanediol diglycidyl ether within such aqueous solution may differ depending on the intended application and/or the type of collagenous tissue to be cross linked. In many applications, concentrations of approximately 4% (v/v) will be usable. The pH of the solution should be maintained at either an acidic or a basic pH in order to facilitate the opening of the epoxy moiety to form a reactive moiety for cross-linking with the tissue functional group. The pH of the solution is maintained at a pH of preferably 3–6, or preferably 8–11, most preferably pH 9.5+/−0.5.

The following are examples of methods by which the presently preferred compound can be utilized in the solution of the present invention to chemically cross link certain types of collagenous biomaterial, to thereby form preserved, surgical implantable bioprostheses.

EXAMPLE II (Preparation of a Pericardial Heart Valve Prosthesis)

A. Harvesting and Preparation of Pericardial Tissue

Bovine pericardial sacs were removed from donor animals and cut into pericardial tissue segments of desired size and shape. Each pericardial tissue segment was thoroughly cleaned with sterile saline solution and any excess or surrounding connective tissue or fat was trimmed away.

B. Preparation of Test Solutions

Four (4) percent (v/v) aqueous solutions of 1,4-butanediol diglycidyl ether, Denacol EX 313 (Nagase Chemicals Ltd., Osaka, Japan) and Denacol EX 810 (Nagase Chemicals Ltd., Osaka, Japan were prepared by mixing the following:

4.46 g sodium carbonate in 180 ml filtered water 0.34 g sodium bicarbonate in 20 ml of filtered water 760 ml filtered water 40 ml 1,4-butanediol diglycidyl ether or 40 ml Denacol EX 313 or 40 ml Denacol EX 810

The pH of the solutions was maintained at 9.5+/−0.5. Each of these test solutions was placed in a separate container.

C. Fixing of the Pericardial Tissue

The segments of pericardial tissue were mounted on suitable tissue-holding fixtures to maintain their desired shape or orientation during the fixation process. The pericardial tissue segments, with their accompanying mounting fixtures, were then separated into groups, and each group of tissue segments was completely immersed in one of the test solutions (i.e., 1,4-butanediol diglycidyl ether, Denacol Ex-313 or Denacol Ex-810) leaving ¼ inch of solution head. The pan was placed on a mechanical shaker and let shake for 3 hours. The test solutions were maintained at room temperature. The stainless steel bars were then removed from the tissues, and the pans were covered to minimize evaporation. Tissue segments were then removed from the Denacol Ex-810 bath after 72 and 144 hours of exposure, and from the 1,4-butanediol diglycidyl ether and Denacol Ex-313 baths after 24, 48 and 144 hours of exposure. At the end of the fixation period, tissues were stored in 30% ethanol.

Following fixation, the pericardial tissue segments were subjected to ninhydrin assays to determine the concentration of free amino groups present in each. The results of these ninhydrin assays were as follows:

| TEST SOLUTION (4% v/v) | EXPOSURE TIME (Hrs. @ room temp.) | FREE AMINE GROUPS DETERMINED BY NINHYDRIN ASSAY (mole $NH_2$/mole collagen) |
| --- | --- | --- |
| 1,4-butanediol diglycidyl ether | 24 | 7.4 |
|  | 48 | 6.5 |
|  | 144 | 2.2 |
| Denacol Ex-313 | 24 | 14.1 |
|  | 48 | 10.8 |
|  | 144 | 4.0 |
| Denacol Ex-810 | 72 | 7.6 |
|  | 144 | 4.6 |

The results of these ninhydrin assays indicate that, after 144 hours of exposure, the completeness of collagen cross linking accomplished by the 1,4-butanediol diglycidyl ether of the present invention was significantly greater than that accomplished by either Denacol Ex-313 or Denacol Ex-810.

D. Fabrication of Pericardial Heart Valve Prostheses

The fixed segments of pericardial tissue were removed from their fixtures, dicut into heart valve leaflet shapes, and attached by way of sutures, to pericardial aortic valve stents, in accordance with known methodology for manufacturing of such bovine pericardial heart valves.

It was subjectively noted that the pericardial tissue cross linked with the 1,4-butanediol diglycidyl ether compound of the present invention was easier to handle and more easily sutured to the valve stent than were the pericardial tissues which had been cross linked by either Denacol Ex-313 or Denacol Ex-810.

E. Storage of Pericardial Heart Valve Prostheses

The pericardial heart valve prostheses which incorporate leaflets formed from the tissue which had been fixed in the 1,4-butanediol diglycidyl ether of the present invention were subsequently stored by immersion in the 4% (v/v) aqueous 1,4-butanediol diglycidyl ether for periods of 1, 2 and 6 days. The shrinkage temperatures of these fixed pericardial tissue leaflets were determined after 1, 2 and 6 days of storage in the 1,4-butanediol diglycidyl ether solution. The shrinkage temperatures of these fixed pericardial tissue leaflets were 77° after 1 day of storage, 77° C. after 2 days of storage and 76° C. after 6 days of storage. These relatively stable shrinkage temperatures indicate that the properties of the fixed pericardial tissue remained substantially unchanged during 6 days of storage in the 4% 1,4-butanediol diglycidyl ether solution of the present invention.

EXAMPLE III (Comparison of the 1,4-butanediol diglycidyl ether fixative of the Present Invention to Denacol Ex-810)

The preferred fixative of the present invention as described in Example I hereabove, is advantageous in that it has a simple molecular structure, which enables such compound to be synthesized in a highly pure form. Furthermore, the molecular weight, size, and reactivity of the 1,4-butanediol diglycidyl ether compound promotes rapid intramolecular cross linking of collagenous tissues in a manner which imparts desirable physical and chemical properties to the cross linked tissue graft. Also, the 1,4-butanediol diglycidyl ether compound of the present invention is highly soluble in an aqueous environment, thereby avoiding the need for the addition of potentially toxic organic solvents to the fixative solution.

In this example, the 1,4-butanediol diglycidyl ether described in Example 1 hereabove and Denacol™ 810 (Nagase Chemicals, Ltd., Osaka, Japan) were subjected to thin layer chromatography using a Whatman K6 60 Å Silica TLC Plate of 250 μm thickness. A chloroform-methanol mixture (95%/5% v/v) was used as the carrier solvent and iodine vapor was used as the visualization reagent.

FIG. 1 shows a comparison of the thin layer of chromatographs of these compounds, indicating that the 1,4-butanediol diglycidyl ether compound of the present invention exhibits high resolution and purity compared to that of Denacol™ 810.

Also, in this example, the 1,4-butanediol diglycidyl ether of Example I was compared to Denacol™ 810 (Nagase Chemicals, Ltd., Osaka, Japan) by gel permeation chromatography (GPC) (also known as size exclusion chromatography (SEC)). A Perkin Elmer 250 binary L.C. pump, equipped with a Hewlett Packard Series 1050 Autosampler was used in this example, with four (4) 30 cm ultrastyragel columns, 500 Å, 100 Å, 50 Å and 50 Å respectively, connected in series to increase the resolution of the gel permeation chromatogram. Quantities of 1,4-butanediol diglycidyl ether and Denacol™ 810 were dissolved in tetrahydrofuran (THF) to concentrations of 0.5%. The mobil phase was THF. The flow rate was 1.0 ml/min. The injection volume was 100 μl. The temperature of each column was controlled at 35° C. during this experiment.

Figure 2:
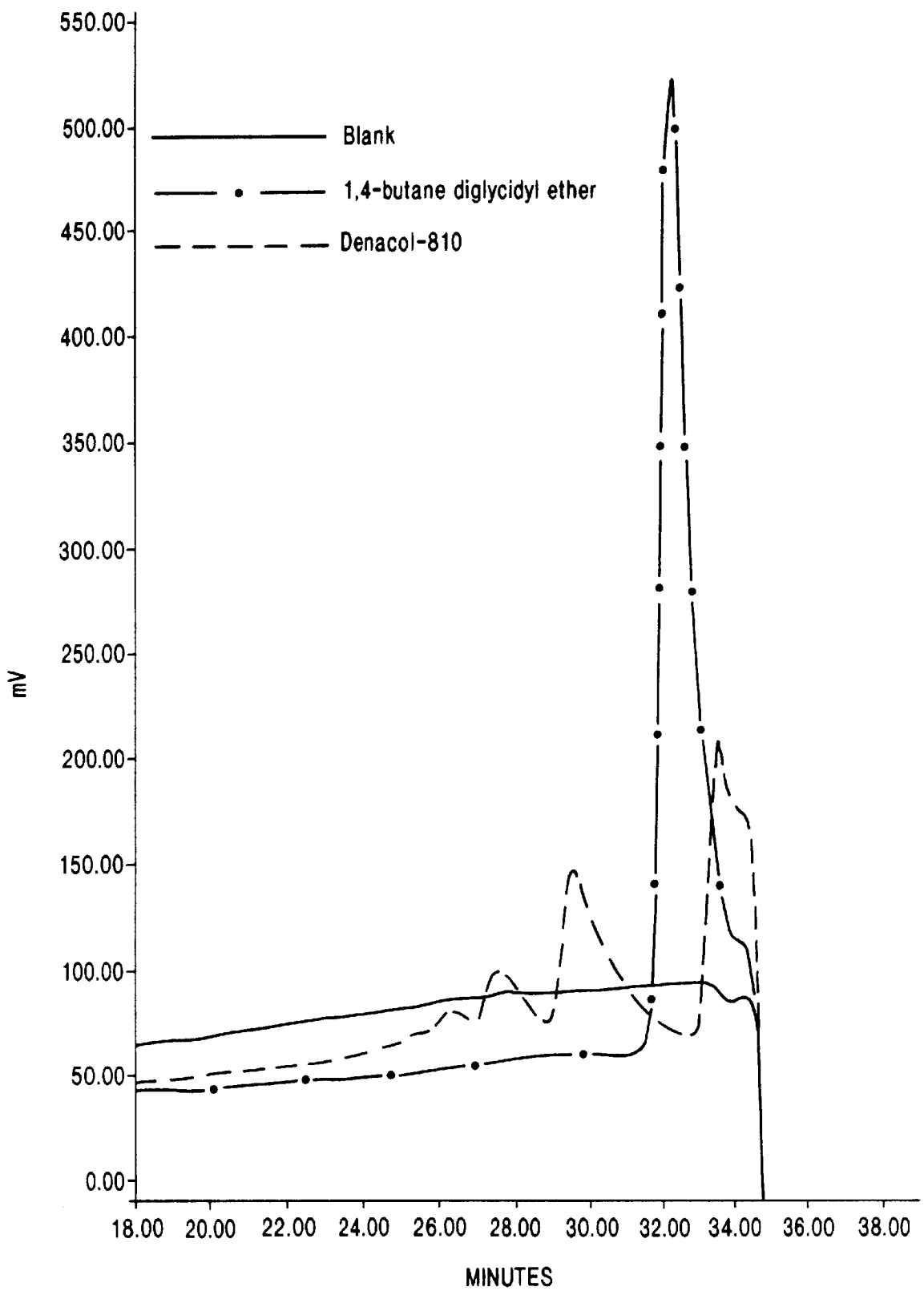
FIG. 2 is a gel permeation chromatogram comparing the 1,4-butanediol diglycidyl ether of the present invention and Denacol™ 810.

FIG. 2 shows the GPC comparison scan of a) 1,4-butanediol diglycidyl ether b) Denacol™ 810 and c) the solvent used. As shown, multiple peaks were present at various molecular weights with Denacol™ 810, while only a single peak was observed with 1,4-butanediol diglycidyl ether. This confirms that the 1,4-butanediol diglycidyl ether preparation of the present invention consists substantially of a single chemical compound and is devoid of impurities, congeners and/or other chemical compounds which could react with collagen, or which could react with the 1,4-butanediol diglycidyl ether itself.

Those skilled in the art will appreciate that the present invention has been described hereabove with reference to certain presently preferred embodiments or examples only, and no effort has been made to exhaustively describe or list all possible embodiments in which the invention may be practiced. Indeed, various additions, deletions, modifications and alterations may be made to the above-described specific embodiments and examples without departing from the intended spirit and scope of the invention. Accordingly, it is intended that all such additions, deletions, modifications and alterations be included within the scope of the following claims.

What is claimed is:

1. A biological tissue graft comprising a collagen-containing tissue which has been cross linked by immersion in a solution comprising a fixative compound having the general formula:

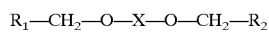

wherein, the molecular backbone X is an aliphatic hydrocarbon having a straight carbon chain consisting of at least four and no more than five carbon atoms bonded directly to one another, said straight carbon chain being devoid of side branches and having terminal carbon atoms at either end thereof, the terminal carbon atoms at the ends of said straight carbon chain being bonded to the oxygen atoms shown in general formula, wherein at least one of the terminal groups $R_1$, $R_2$ is an epoxy group and the other of the such terminal groups $R_1$, $R_2$ is either a) an epoxy group, or b) an aldehyde group, said solution being substantially devoid of additional chemical compounds that react with collagen or with said fixative compound during cross linking.

2. The biological tissue graft of claim 1 wherein said collagen containing tissue comprises a mammalian heart value.

3. The biological tissue graft of claim 1 wherein said collagen containing tissue comprises a mammalian cardiovascular valve.

4. The biological tissue graft of claim 1 wherein said collagen containing tissue comprises a segment of blood vessel.

5. The biological tissue graft of claim 1 wherein said collagen containing tissue comprises a tendon.

6. The biological tissue graft of claim 1 wherein said collagen containing tissue comprises skin.

7. The biological tissue graft of claim 1 wherein X is a straight chain aliphatic hydrocarbon of four carbon atoms bonded directly to one another.

8. The biological tissue graft of claim 1 wherein X is a straight chain aliphatic hydrocarbon selected from the group consisting of n-butyl and n-pentyl.

9. The biological tissue graft of claim 1 wherein both $R_1$ and $R_2$ are epoxy groups.

10. The biological tissue graft of claim 1 wherein one of $R_1$ and $R_2$ is an epoxy group and the other is an aldehyde group.

11. The biological tissue graft of claim 1 wherein said compound is soluble in aqueous solution at concentrations of at least 4% (v/v).

12. The biological tissue graft of claim 1 wherein said compound is soluble in aqueous solution at concentrations of at least 10% (v/v).

13. The biological tissue graft of claim 1 wherein said compound is 1,4-butanediol diglycidyl ether.

* * * * *